United States Patent [19]

Sundberg

[11] Patent Number: 5,494,044
[45] Date of Patent: Feb. 27, 1996

[54] METHOD FOR TAKING A SAMPLE OF AMNIOTIC FLUID

[75] Inventor: Karin Sundberg, Hellerup, Denmark

[73] Assignee: Amnitec A/S, Soberg, Denmark

[21] Appl. No.: 243,613

[22] Filed: May 6, 1994

Related U.S. Application Data

[63] Continuation of Ser. No. 784,419, Dec. 23, 1991, abandoned.

[30] Foreign Application Priority Data

May 10, 1989 [DK] Denmark ................................. 2293/89

[51] Int. Cl.$^6$ .............................................. A61B 5/00
[52] U.S. Cl. ............................ 128/749; 128/760; 128/763; 604/55; 604/190
[58] Field of Search ............................ 128/749, 750, 128/752, 753, 760, 763, 765, 766, 775; 604/27, 28, 55, 187, 190, 218, 406; 606/125; 210/416.1, 418, 448

[56] References Cited

U.S. PATENT DOCUMENTS

| | | | |
|---|---|---|---|
| 3,224,434 | 11/1962 | Molomut et al. | 128/760 |
| 3,938,513 | 2/1976 | Hargest | 604/190 |
| 4,066,079 | 1/1978 | Chiarolla | 604/190 |
| 4,194,513 | 3/1980 | Rhine et al. | 128/750 |
| 4,280,508 | 7/1981 | Barrada | 128/736 |
| 4,308,875 | 1/1982 | Young | 128/753 |
| 4,366,822 | 1/1983 | Altshuler | 128/753 |
| 4,685,472 | 8/1987 | Muto | 128/760 |
| 4,807,625 | 2/1989 | Singleton | 604/55 |
| 4,820,276 | 4/1989 | Moreno | 604/190 |
| 4,957,629 | 9/1990 | Smith et al. | 604/406 |
| 5,000,192 | 3/1991 | Sealfon | 128/760 |
| 5,015,369 | 5/1991 | Romine et al. | |

*Primary Examiner*—Stephen C. Pellegrino
*Assistant Examiner*—Guy V. Tucker
*Attorney, Agent, or Firm*—Merchant, Gould, Smith, Edell, Welter & Schmidt

[57] ABSTRACT

A sample of amniotic fluid containing cells may be taken out from the amniotic cavity by penetrating the wall of the amniotic cavity by means of a hollow needle (15) through which a volume of the amniotic fluid may be withdrawn. Outside the amniotic cavity the cells or part thereof are separated from the amniotic fluid which is immediately thereafter returned to the amniotic cavity. This means that it is possible to withdraw a relatively large amount of cells without considerably reducing the total volume of the amniotic fluid present in the amniotic cavity. Therefore, it is possible to take out a sample at an early stage of pregnancy period. The sample may, for example, be withdrawn by means of a sampling device comprising a one-way valve (16, 17) including a cell filter (17). The sampling device may further comprise a syringe with cylinder (10) and a piston (11) movably arranged therein. By moving the piston (11) through a suitable number of consecutive suction and pressure strokes a suitable amount of cell material is deposited on the cell filter (17). The filter (17) may be withdrawn from the sampling device and the cells may be cultured on the cell filter or the cells may be flushed from the filter by means of a culturing medium.

9 Claims, 2 Drawing Sheets

METHOD FOR TAKING A SAMPLE OF AMNIOTIC FLUID

This is a continuation, of application Ser. No. 07/784419, filed 23 Dec. 1991, now abandoned.

TECHNICAL FIELD

The present invention relates to a method of taking out a sample of a cell-containing amniotic fluid from an amniotic cavity, said method comprising penetrating the wall of the amniotic cavity by means of a hollow needle or cannula and extracting a volume of cell-containing amniotic fluid therethrough.

BACKGROUND

In some countries sampling of amniotic fluid is offered to pregnant women having an increased risk of bearing children with chromosome disorders. If the sample collected indicates that the child to be born is diseased an induced abortion is offered.

With the presently applied sampling technique 15–20 ml amniotic fluid is collected in the 16th week of pregnancy, and normally a further 3–4 weeks elapse before a result of the laboratory examination is available. Consequently, the pregnant woman in most cases will be in the 19th–20th week of pregnancy before an abortion can be induced. Of course this represents a heavy strain for the woman at this advanced stage of pregnancy and also from a medical point of view it is inappropriate.

With the present technique it is not possible to carry out the sampling of amniotic fluid earlier, since this involves a considerable risk that the collected sample fails to give the desired result due to a too low content of cells. When routine amniocentesis is carried out approximately 10% of the total volume of the amniotic fluid is collected. It has been shown that if more than 17 ml is collected in the 16th week of pregnancy, the risk of respiratory distress in the neonatals is increased (Jo-Anne K. Finegan, 1984). Thus, the motivation for collecting samples at this late stage of pregnancy has been to achieve a successful culturing of cells and partly to avoid the risk of spontaneous abortion which risk is known to be relatively low at this stage (A. Tabor, Thesis, 1988).

During recent years, chorionic villi biopsy has been developed in order to obtain early chromosomal examinations of the fetus. By this technique, it is normally possible to obtain a result in the late first trimester. However, this method of sampling involves the problem that the placenta tissue is not always chromosomally identical with the fetus which is a prerequisite for a correct diagnosis (Verjaal M. et al., 1987; Eiben B. et al., 1989). Consequently, it is necessary to carry out amniocentesis in a significant number of pregnant women in the 16th pregnancy week in order to determine whether the diagnosis is correct or not, since amniocentesis is still the most reliable method for chromosomal examinations of fetuses. Furthermore, chorionic villi biopsy is an expensive examination. It is estimated that a chorionic villi biopsy sample requires the double number of technician hours to be processed when compared to an amniotic fluid sample.

It is therefore of considerable relevance to improve the amniocentesis technique. Preliminary results from USA indicate that amniocentesis carried out at an early stage, even as early as the 9th week of pregnancy, implies a low risk of spontaneous abortion, and that the risk of complications at later stages of the pregnancy does not seem to be increased (Hanson F. W. et al., 1987; Elejalde B. R. and Elejalde M. M., 1988; Goodmilow L. et al., 1988).

With the presently used technique, only the cells in a sample of amniotic fluid are used for chromosomal fetus examination. After centrifugation of the sample, the supernatant is discarded, so that only the cells remain. Subsequently, these cells are cultivated for 2–3 weeks in order to obtain a sufficient number of dividing cells for the chromosomal examination. Only 2 ml of amniotic fluid is used for alpha-fetoprotein determination, and this part of the amniocentesis is independent of the concentration of cells. The cells in the amniotic fluid are considered to be waste products without any significance for the development of the fetus.

The present invention provides a method of the above type and the method according to the invention is characterized in separating outside the amniotic cavity amniotic fluid with a reduced content of cells from the extracted volume of amniotic fluid and recirculating at least part of the separated fluid to the amniotic cavity substantially immediately after the separation, whereby a sample with an increased cell concentration is retained.

Because the separated amniotic fluid with reduced content of cells is substantially immediately returned to the amniotic cavity, a sample containing the necessary amount of cells may be collected by permanently removing only a relatively small volume of amniotic fluid from the amniotic cavity. Because of the relatively small volume of amniotic fluid necessary the sample collection can be carried out at an earlier stage of pregnancy without an increase of the abortion risk and even with a reduced risk of abortion.

Since the cells in the amniotic fluid are considered to be waste products which may be removed from the amniotic cavity without any risk increase the method according to the invention renders it possible to collect a sample containing a relatively large amount of cell material. This means that the necessary time for carrying out the laboratory examination may be reduced, because the cell material may be cultivated in a time period which is shorter than hitherto.

It is primarily the relative amount of amniotic fluid being removed from the amniotic cavity which is decisive for how early in the pregnancy period a sample can be collected. In the method according to the invention the amniotic fluid removed from the amniotic cavity may be separated continuously and the separated amniotic fluid with its reduced cell content may then simultaneously and continuously be returned to the amniotic cavity through a return passage. This means that in principle a rather considerable part of the cell material present within the amniotic cavity may be removed therefrom while only a rather small amount of amniotic fluid is present outside the amniotic cavity at any time.

Alternatively the volume of amniotic fluid may be withdrawn from the amniotic cavity in two or more part volumes and after the withdrawal of each of these volumes the separation and the subsequent recirculation of amniotic fluid to the amniotic cavity may be take place before the next part volume is withdrawn or taken out. Consequently only one part volume is removed from the amniotic cavity at a time and the amount of fluid present in such part volume may then be adapted to the total amount of amniotic fluid present in the amniotic cavity at the time when the sample is to be taken out, whereby the risk may be reduced to an acceptable level.

The separation of amniotic fluid with a reduced content of cells may be performed in any suitable manner, for example by centrifuging. However, the separation is preferably performed by filtration by passing at least part of the volume of amniotic fluid withdrawn from the amniotic cavity through a cell filter which may be arranged at a suitable position within the flow passage of the amniotic fluid outside the amniotic cavity. Thus, part of the cells present in the amniotic fluid will be filtered from the fluid and be retained by the filter. The amniotic fluid having flown through the filter whereby its content of cells has been reduced may then continuously or intermittently be returned to the amniotic cavity. The cells which are filtered from the amniotic fluid and which are deposited on the filter may be removed together with the cell filter and subsequent cultivation of the cells may take place on the filter. Such a procedure involves a substantial saving of time and rationalization in cultivating the cell material.

The volume of amniotic fluid may be withdrawn from the amniotic cavity in any suitable manner. As an example, the amniotic fluid may be continuously withdrawn from the amniotic cavity and recirculated thereto through an external flow passage through which the fluid is circulated by means of a peristaltic pump or another kind of pump In the preferred embodiment, however, the volume of amniotic fluid is withdrawn from the amniotic cavity by means of a syringe, and amniotic fluid is then drawn or sucked into a chamber defined within the syringe and thereafter displaced from the syringe chamber and returned to the amniotic cavity, the amniotic fluid being passed through a cell filter when the fluid is drawn into or displaced from the syringe chamber. This means that the syringe should be adapted so as to cause the amniotic fluid to flow through the cell filter mainly in one direction.

The invention also relates to an apparatus or sampling device for use in carrying out the method as described above and comprising a hollow needle or cannula for penetrating the wall of the amniotic cavity, a sample receiving chamber communicating with the hollow needle or cannula, and means for drawing a volume of amniotic fluid into the sample receiving chamber through the hollow needle, and the apparatus according to the invention is characterized in that the apparatus further comprises separating means for separating amniotic fluid with a reduced content of-cells from said volume of amniotic fluid drawn into the sample receiving chamber, and fluid returning means for returning at least part of the separated amniotic fluid to the amniotic cavity.

The apparatus or sampling device may be in the form of a syringe and the return means may comprise a one-way valve for causing the amniotic fluid to flow through the cell filter in one direction only during the suction and pressure strokes of the piston of the syringe. Furthermore, the separating means may comprise a cell filter which may form part of the one-way valve. The one-way valve may be adapted to open during the suction stroke of the syringe so that amniotic fluid containing cell material may be sucked into the syringe cylinder through the hollow needle of the syringe. When the syringe piston is subsequently moved in the opposite direction through a pressure stroke the one-way valve closes so as to cause the cell-containing amniotic fluid to be forced through the cell filter arranged within the one-way valve, and the filtered amniotic fluid with a reduced cell content may then be returned to the amniotic cavity through the hollow needle. After the pressure stroke of the syringe piston cell material deposited on the cell filter and a small residual volume of fluid are left in the syringe. The residual amount of amniotic fluid may be used for alpha-fetoprotein determination. In order to avoid excessive sudden changes in pressure within the amniotic cavity small amounts of amniotic fluid may be sucked into the syringe at a time. Thus, the syringe piston may be moved through a number of short consecutive suction and pressure strokes. In this manner a substantial amount of cells may be removed from the amniotic fluid with a rather small physical influence of the pregnancy. When the filter material within the syringe has been filled with cells the resistance against the piston movements will increase and the sampling procedure may then be terminated. In case of amniocentesis at a late stage of pregnancy it may possibly be preferred to use a single relatively long suction stroke and a subsequent corresponding pressure stroke. After sampling the cells filtered from the amniotic fluid may be rinsed off the cell filter with culturing medium directly into a culturing flask whereby centrifugation of the sample is unnecessary. Alternatively, the cells may be cultivated directly on the filter as mentioned above.

Summarizing, the following advantages may be obtained by the method and apparatus according to the invention:

a) The collection of the samples can be carried out at an earlier stage of pregnancy due to the fact that an increased number of cells results in better cell growth.

b) The time required to obtain results is reduced considerably.

c) The system implies more independence as regards a specific stage of pregnancy at the time of sample collection, since the collection of sample may be continued until the resistance from the filter is increased so as to indicate that a sufficient number of cells has been collected.

d) The risk of inducing abortions due to the sample collection may be decreased, since only a very small proportion of the amniotic fluid is permanently removed from the amniotic cavity, whereby the conditions of pressure remain substantially unchanged in the amniotic cavity.

e) The risk of amniotic banding/amniotic prolapse leading to congenital malformations or abortions may be decreased by carrying out amniocentesis at the above early stage since the cell membranes are not adherent until the 10th–12th week of pregnancy.

f) The risk of developing lung complications in the newborns may also be reduced, since several studies have indicated a connection between the amount of amniotic fluid at the time of sampling collection and the risk of developing lung problems (Jo-Anne Finegan, 1984).

g) An increased proportion of living cells in the sample as compared to the presently used technique where only approximately 10% of the cells in the 16th week of pregnancy are alive. It is assumed that it is possible to obtain this larger proportion of living cells since the recirculation of amniotic fluid results in a larger fluidal flow around the needle point whereby an increased number of vital cells will be detached from the fetus and the membranes.

h) A reduction of non-successful samplings due to lack of cell growth since each individual sample will contain a large number of cells. (D. E. Rooney et al., 1989).

i) The costs involved in amniocentesis as compared to chorionic villi biopsy are lower.

j) An increased number of cell clones from which chromosomal analysis can be carried out will result in a more reliable chromosomal diagnosis as compared to the present situation where an answer in some cases is to be given on the basis of only 5 clones.

k) An improved diagnosis of chromosomal mosaicism due to the presence of more cells in the starting material.

BRIEF DESCRIPTION OF THE DRAWINGS

The invention will now be further described with reference to the drawings, wherein.

DETAILED DESCRIPTION OF THE PREFERRED EMBODIMENTS

Figure 1:
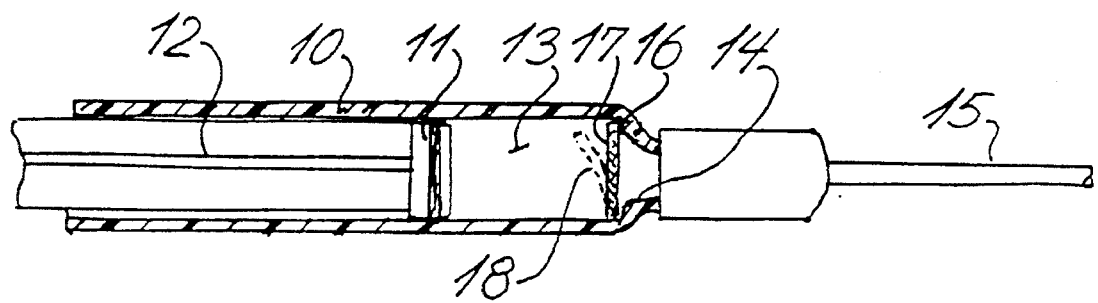
FIG. 1 is a diagrammatic side view and partial sectional view illustrating a first embodiment of a syringe or sampling device according to the invention.

The syringe or sampling device shown in FIG. 1 comprises a cylinder 10 having a piston 11 with a piston rod 12 displaceably mounted therein. Within the cylinder 10 the piston 11 defines a cylinder chamber 13 having a volume which may be changed by displacing the piston 11. The cylinder 10 comprises at one end a cone or needle seat 14 for mounting a hollow needle or cannula 15. An annular shoulder 16 is defined within the cylinder 10 at the end of which the cone 14 is formed, and a cell filter 17 is mounted on the shoulder 16. The cell filter 17, which is fluid penetrable, but able to retain amnion cells is formed like a valve flap which may be moved between an open position indicated by dotted lines 18 in FIG. 1 and a closed position in which the peripheral portion of the filter is in engagement with the shoulder 16.

When a sample of amniotic fluid is to be taken out from the amniotic cavity by means of the syringe shown in FIG. 1 the piston 11 is in its advanced position in which it is in abutting engagement with the cell filter 17. The pointed end of the hollow needle 15 is now passed through the wall of the amniotic cavity while the insertion of the needle is surveyed by ultrasound scanning. When the wall of the amniotic cavity has been penetrated by the hollow needle the piston 11 is moved outwardly during a suction stroke whereby cell containing amniotic fluid flows through the hollow needle 15 into the cylinder chamber 13 while the valve flap or cell filter 17 is in its open position indicated by dotted lines 18. When a sufficiently small amount of cell-containing amniotic fluid has been sucked into the cylinder 10 the piston 11 is pressed towards its advanced position whereby the fluid sucked into the cylinder chamber is again displaced therefrom through the hollow needle 15 and returned to the amniotic cavity. During the pressure stroke the valve flap or cell filter 17 closes automatically so that the cell-containing amniotic fluid is pressed through the filter whereby a substantial part of the cells in the fluid is filtered therefrom and remains on the inner side of the filter, and the amniotic fluid which is returned to the amniotic cavity has a substantially reduced content of cells. The procedure may be repeated one or several times if desired so that a small amount of amniotic fluid is once more sucked into the cylinder and subsequently returned to the amniotic cavity. When a suitable amount of cell material has been collected on the inner side of the cell filter 17, which functions as a one way valve, the sampling procedure is terminated and the hollow needle is withdrawn from the wall of the amniotic cavity. A possible small residual amount of amniotic fluid present within the cylinder chamber 13 when the piston 11 is in its advanced position may be used for alpha-fetoprotein determination, if desired. The filter 17 with the amniotic cells deposited thereon may now be removed from the syringe and the cells may be rinsed, if desired.

If the piston is moved only a very short length during the sampling so that the suction stroke as well as the pressure stroke are rather short it is possible to withdraw only a very small amount of fluid from the amniotic cavity at a time. This means that a cell containing amniotic fluid sample may be collected at a rather early stage of the pregnancy period when the total amount of fluid in the amniotic cavity is relatively small, without the risk of any substantial adverse influence.

Figure 2:
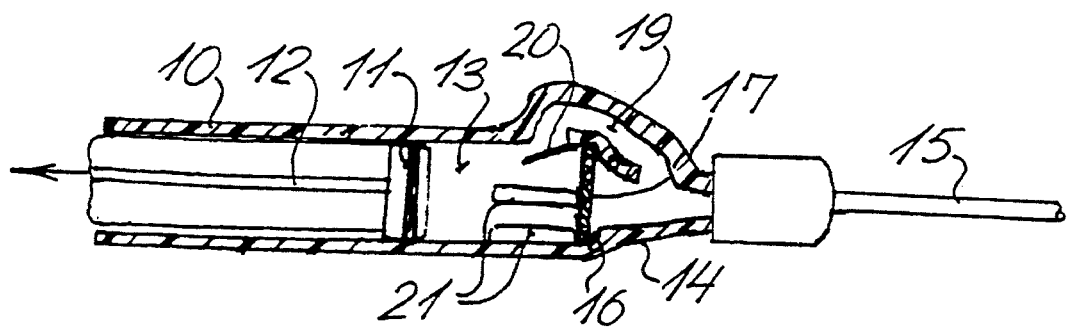
FIG. 2 is a side view and partial sectional view of a second embodiment of the sampling device according to the invention.

FIG. 2 shows a modified embodiment of the syringe according to the invention. In the embodiment shown in FIG. 2 the cell filter 17 is fastened to the shoulder 16, and the inner bore of the cone 14 communicates with the cylinder chamber 13 not only through the cell filter 17, but also through a by-pass passage 19. The by-pass passage is controlled by a one-way valve or non-return valve 20 allowing fluid to flow through the by-pass passage 19 in a direction from the cone 14 and into the cylinder chamber 13, but not in the opposite direction. One or more abutment fins 21 may be formed on the inner surface of the cylinder, and the outer ends of these fins may determine the innermost position of the piston 11 and may prevent the piston from coming into contact with the one-way valve 20.

The syringe shown in FIG. 2 may be used in substantially the same manner as described above in connection with FIG. 1. During the suction stroke of the piston 11 the one-way valve 20 is open as shown in FIG. 2, and the main part of fluid sucked into the syringe will flow into the cylinder chamber 13 through the by-pass passage 19 where the flow resistance is smallest. During the pressure stroke of the piston the one-way valve 20 is closed so that the fluid is forced to flow out from the cylinder chamber 13 through the cell filter 17 whereby the outflowing fluid is filtered. After a suitable number of successive suction and pressure strokes the cell filter 17 with the filtered amniotic cells is removed, and these cells may then be cultivated as described above.

Figure 3:
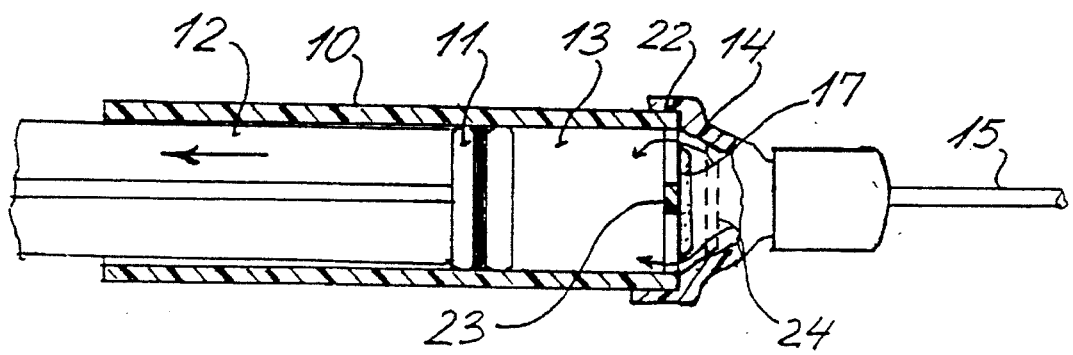
FIG. 3 is a side view and partial sectional view showing a third embodiment of a sampling device according to the invention.

The embodiment of the syringe shown in FIG. 3 corresponds to that shown in FIG. 1 apart from the fact that the cell filter 17 in FIG. 1 is formed like a flap which also functions as a one-way valve, while the cell filter 17 in FIG. 3 is loosely arranged within the cone 14 which is a separate part. The separately formed cone 14 may be releasably fastened to the adjacent end of the cylinder 10 by a frictional fit 22, a thread connection, a bayonet socket or another releasable connection. The filter 17, which may, for example, be filter material which is surrounded by a grid-shaped or perforated stiff housing, has a diameter which is somewhat smaller than the inner diameter of the cylinder 10 and the filter 17 is prevented from penetrating into the cylinder 10 by an abutment means 23 which may, for example, be a cruciformed member as shown in FIG. 3.

During the suction stroke the cell filter 17 is moved into abutting engagement with the abutment means 23 as shown in FIG. 3, but the fluid sucked into the syringe may freely flow into the cylinder along the periphery of the filter 17 as indicated by arrows in FIG. 3. During the pressure stroke the filter 17 is moved away from the abutment means 23 so that the circumferential part thereof is pressed into abutting engagement with the inner wall of the cone 14 as indicated by dotted lines 24 in FIG. 3. That means that the cell-containing amniotic fluid displaced from the cylinder chamber 13 during the pressure stroke is forced to pass the cell filter 17 whereby a substantial part of the cells is filtered from the amniotic fluid. When a sufficient amount of cells has been collected on the filter 17 after two or more pressure and suction strokes, the sampling procedure may be terminated and the cone 14 may be removed from the cylinder 10 by releasing the connection 22. The filter 17 with the cell material filtered from the amniotic fluid may now easily be removed.

Figures 4, 5, 6:
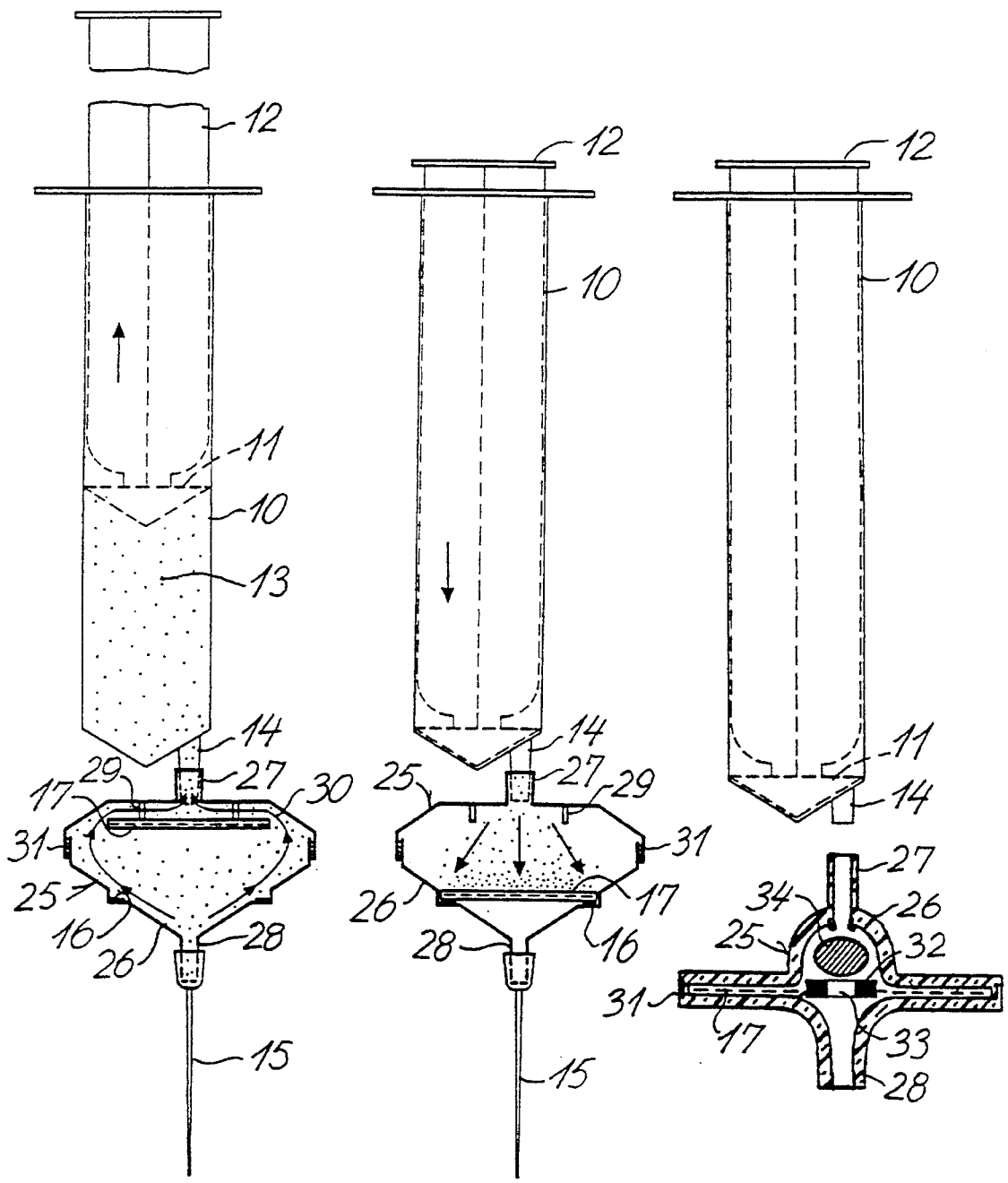
FIG. 4 and 5 are diagrammatic side view showing a fourth embodiment of a sampling device according to the invention and illustrating the device during suction and pressure strokes, respectively.
FIG. 6 is a diagrammatic side view illustrating a fifth embodiment of a syringe according to the present invention.

FIGS. 4 and 5 illustrate a sampling syringe or sampling device comprising a standard amniocentesis syringe and a standard needle 15. The device further comprises a filtering unit 25 having a housing 26 with an outwardly extending socket 27 for receiving the cone 14 of the syringe cylinder 10 and an oppositely directed cone 28 for mounting the needle 15 thereon. The filtering unit 25 may be of the disposable type delivered in a sterilized package. A plate or disc-like filtering member 17 is arranged within the housing 26 so as to be freely movable between a first position in which the filtering member is in abutting engagement with an inner annular shoulder formed in the housing 26 (FIG. 5) and an open position in which the filtering member is in abutting engagement with spacer members 29 projecting into the housing from an inner wall part adjacent to the socket 27 (FIG. 4). The filtering member may comprise a filtering medium which is sandwiched between a pair of opposite, perforated disc members.

The sample device or syringe illustrated in FIGS. 4 and 5 may be operated as follows: When the piston 11 is in its innermost position as shown in FIG. 5 and the pointed end of the hollow needle 15 has been inserted through the wall of the amniotic cavity as described above, the piston 11 may be moved outwardly as indicated by an arrow in FIG. 4, whereby amniotic cell-containing fluid is sucked into the housing 26 of the filtering unit 25. The fluid flow through the housing 26 moves the filtering member 17 to its open position as shown in FIG. 4 so that the fluid may freely flow through the housing 26 and through the cone 14 into the cylinder chamber 13 as indicated by arrows 30 in FIG. 4. When a desired amount of amniotic fluid has been sucked into the cylinder chamber 13, the movement of the piston 11 is reversed as indicated by an arrow in FIG. 5 so as to expel the fluid from the syringe chamber 13. When fluid is discharged from the syringe chamber 13 through the pressure stroke the fluid flow through the housing 26 from the cone 14 to the needle 15 causes the filtering disc 17 to move to its closed position as shown in FIG. 5. The annular shoulder 16 may be provided with an annular sealing member, such as a sealing ring made of silicon, so as to provide a tight engagement between the peripheral part of the filtering disc 17 and the shoulder 16. Consequently, fluid expelled from the syringe chamber 13 is forced to flow through the filtering member 17 whereby amniotic cells are filtered from the fluid and deposited on the filtering member 17 while the filtered fluid having a reduced cell content is returned to the amniotic cavity through the needle 15. The suction-expulsion procedure described may now be repeated several times and the amount of cell material retained by the filter member is increased each time amniotic fluid is circulated through the sampling device. A substantially increased flow resistance during the pressure stroke indicates that a sufficient amount of cell material has been retained by the filter member 17, and the sampling may then be terminated. When the needle 15 has been retracted from the amniotic cavity, the filtering unit 25 may be removed from the cone 14 of the syringe. Thereafter, a culturing medium may be sucked into the syringe. The housing 26 is composed by two separate parts which are releasably interconnected for example by means of a screw connection 31, and the housing parts may now be disconnected by releasing the connection 31. Now, the filtering member 17 is turned around, for example by means of pincers, whereafter the housing members are reconnected by means of the screw connection 31 and the socket 27 is remounted on the cone 14. Now, the culturing medium may be expelled from the syringe chamber 13 through the housing 26 and through the filtering member 17 which is in its closed position as shown in FIG. 5. Thus, the filtering member 17 is flushed by the culturing medium and the amniotic cells retained by the filtering member is removed therefrom and entrained by the culturing medium. The culturing medium containing the filtered cell material may be discharged directly into a culturing flask which may be placed in an incubator. In this manner the tedious centrifugation procedure used in the conventional technique may be avoided.

In cases where the collected sample of cell material is not to be cultivated immediately after the sampling procedure but is to be sent to a laboratory, the filtering unit 25 may be removed from the syringe and the needle 15 may be removed from the housing 26. Thereafter, the socket 27 and the cone 28 may be plugged or otherwise closed by means of suitable closing means. The small amount of amniotic fluid present in the filtering unit 25 is sufficient to keep the cells alive during transportation or mailing.

FIG. 6 shows a modified embodiment of the sampling device shown in FIGS. 4 and 5. In the embodiment shown in FIG. 6 the filtering member 17 is mounted substantially stationarily within the housing 26 of the filtering unit 25, and the filtering member comprises a central ring 32 defining a central opening 33 and forming a valve seat for a valve body 34, which may, for example, be a ball-like member made from plastic material. The valve body 34 cooperates with the annular valve seat 32 so as to form a one-way valve allowing fluid to flow through the central opening 33 when amniotic fluid is sucked into the syringe 10 through the housing 26. On the other hand, when fluid is expelled from the syringe the one-way valve closes the opening 33 whereby the amniotic fluid being expelled is forced to flow through the filter member 17. Otherwise, substantially the same sampling procedure as described above may be used in connection with the sampling device shown in FIG. 6. The housing 26 may consist of two separate parts interconnected by a releasable connection, such as a screw connection 31 and the cell material retained by the filtering member 17 may then be flushed from the filtering member in a manner similar to that described above.

Type of filter and size of pores therein

In order to find the best cell filtering material a test has been made with cellulose filters having different size of pores, namely 1.2 µm, 3 µm, 5 µm and 8 µm. Fluid containing cultured amnion cells in concentrations corresponding to the concentrations of untreated amniotic fluid samples was filtered. The smallest cells in an amniotic fluid sample are the living cells and therefore the optimum pore size must be determined on the basis of the smallest cells.

Cultured amnion cells are all alive and therefore they are well suited for such determination of the best size of pores.

A series of amniotic samples which had been cultured for a long time was treated with trypsin EDTA in order to loosen all the cells from the bottom of the culturing flask whereby a suspension containing free floating amnion cells was prepared. This suspension was diluted so as to obtain a concentration of cells comparable to that of an untreated amniotic fluid sample.

By means of a 20 ml syringe of the type normally used for conventional amniocentesis approximately 20 ml of the cell suspension was forced through a cellulose paper filter arranged in a filter holder. The filtered fluid was examined under microscope. During the filtration, the force necessary for expelling the suspension from the syringe was also noticed. The filter diameter was 47 mm. The results of the test are stated in the following table

TABLE

| Size of pores | 1.2 µm | 3 µm | 5 µm | 8 µm |
|---|---|---|---|---|
| Resistance | low | low | low | low |
| Cells in filtrated fluid | none | very few | some | many |

From the above test is was concluded that a filter having a pore size of less than 3 µm are best suited. A pore size of 1.2 µm, for example, is a good size because all of the cells are retained by the filtration and the flow resistance through the filter is low. It was found that with such size of pores 50 mm of the cell suspension could be filtered completely without any appreciable flow resistance. The cells retained by the filter could be flushed from the filter without any problems.

However, cellulose is probably not the most suited material for use in connection with the present invention because this material is to some extend protein binding. Therefore, three different filter materials from Millipore have been examined for toxicity by means of the so-called mouse test in which the ability of mouse embryos to develop from the 2-cell stage to the blastocyst stage is examined. Small pieces of filter material were placed with the mouse embryos and the degree of blastocyst development was evaluated and compared with a control without any additions. The following materials have been tested: Cellulose esters, polycarbonate, polyvinyldifluoride, and the plastic materials of the applied 3-way plugs. All these materials were found non-toxic and it was concluded that the studied materials are applicable. Furthermore, repeated amniotic fluid cultivations have been carried out from pooled amniotic fluid remnants, in which small pieces of filter material have been added to the culturing flasks. The cell growth of these flasks were compared with control cultivations from the same pool. No significant differences in growth were found for the different materials.

By comparative cultivations of small and larger aliquots of amniotic fluid from the same pool, it was shown that the larger volumes of amniotic fluid containing a larger number of cells also results in correspondingly more clones, which is a prerequisite for the new amniocentesis system. In six experimental series from different pools of amniotic fluid unequivocal results from culturing have been found.

After filtration of pooled amniotic fluid remnants the cells were removed from the filters by rinsing with the culturing medium and it was shown that it is possible to grow cells successfully after this filtration procedure. This experiment was carried out using different filter materials and pore sizes. Different filter housings have been applied and varying volumes of amniotic fluid were filtered. The filtration procedure itself implies a very small loss of cells, which does not exceed the loss seen with the presently used procedure of centrifugation. This was examined by using polycarbonate filters which are partially transparent. After filtration the filters were examined for adherent cells by microscopy, and only very few cells were found. The filtered samples were all compared with control samples from the same pool of amniotic fluid which had only been centrifuged. The same number and the same size of clones were obtained, and the cell types were the same for the two procedures.

It should be understood that various changes and modifications of the sampling devices and methods described above could be made within the scope of the present invention. Thus, in principle any sampling device or sampling system by means of which amniotic fluid may be withdrawn from the amniotic cavity filtered outside the amniotic cavity and returned to the amniotic cavity with a more or less reduced content of cells could be used. As an example, the syrings described above need not be provided with a displaceable piston, but the walls of the syringe chamber may be deformable so that the syringe chamber may be compressed.

I claim:

1. A method of taking out a sample of a cell-containing amniotic fluid from an amniotic cavity, said method comprising the steps of:

penetrating the wall of the amniotic cavity by means of a hollow needle, extracting a volume of cell-containing amniotic fluid through the hollow needle, separating outside the amniotic cavity amniotic fluid with reduced content of cells from the extracted volume of amniotic fluid, and returning at least part of the separated fluid to the amniotic cavity immediately after the separation, whereby a sample with an increased cell concentration is retained.

2. A method according to claim 1, wherein the separation is performed continuously while separated amniotic fluid is continuously and simultaneously returned to the amniotic cavity through a return passage.

3. A method according to claim 1, wherein said volume of amniotic fluid is extracted in at least two part volumes, amniotic fluid is being separated from each of these part volumes after extracting same and subsequently returning separated amniotic fluid prior to extracting the next part volume.

4. A method according to claim 1, wherein amniotic fluid is separated by passing at least part of said extracted volume of amniotic fluid through a cell filter.

5. A method according to claim 4, wherein said volume of amniotic fluid is extracted by means of a syringe, amniotic fluid from the amniotic cavity being drawn into a chamber of the syringe and subsequently displaced from said chamber and returned to the amniotic cavity.

6. A method according to claim 5, wherein the cell filter is arranged within a housing of a filtering unit which is removably connected to the syringe and provided with a cone on which the hollow needle is mounted whereby amniotic fluid which is drawn into the syringe chamber and subsequently displaced therefrom is passed through the housing of the filtering unit.

7. A method according to claim 6, further comprising the steps of:

separating the filtering unit from the syringe when the separated fluid has been returned to the amniotic cavity, subsequently drawing a culturing medium into the syringe chamber, reconnecting the filtering unit to the syringe, and expelling the culturing medium from the syringe chamber and through the cell filter in the housing of the filtering unit in a direction so as to flush amniotic cells from the filter by means of the culturing medium.

8. A method according to claim 7, wherein the expelling step includes turning cell filter upside down within the housing of the filtering unit prior to expelling culturing medium through the cell filter.

9. A method according to claim 7, further including the step of flushing the culturing medium containing amniotic cells from the cell filter and collecting same in a culturing flask, placing the flask in an incubator.

* * * * *